United States Patent [19]

Quakenbush

[11] Patent Number: 5,302,763
[45] Date of Patent: Apr. 12, 1994

[54] PROCESS FOR PREPARING DINITROTOLUENE

[75] Inventor: Allen B. Quakenbush, Lake Charles, La.

[73] Assignee: Olin Corporation, Stamford, Conn.

[21] Appl. No.: 24,052

[22] Filed: Mar. 1, 1993

[51] Int. Cl.$^5$ .................................................. C07C 205/11
[52] U.S. Cl. ............................................................. 568/934
[58] Field of Search .............................................. 568/934

[56] References Cited

U.S. PATENT DOCUMENTS

| | | |
|---|---|---|
| 2,362,743 | 2/1943 | Crater .................................. 568/934 |
| 3,928,395 | 12/1975 | Seha et al. ........................... 568/934 |
| 3,957,889 | 5/1976 | Milligan et al. ...................... 568/934 |
| 4,064,147 | 12/1977 | Thelen et al. ........................ 568/934 |
| 4,804,792 | 2/1989 | Mason et al. ......................... 568/934 |
| 4,918,250 | 4/1990 | Mason et al. ......................... 568/934 |
| 4,996,376 | 2/1991 | Doussain et al. ..................... 568/394 |
| 5,001,272 | 3/1991 | Mason .................................. 568/934 |
| 5,099,078 | 3/1992 | Quakenbush ......................... 568/934 |
| 5,099,079 | 3/1992 | Quakenbush ......................... 568/934 |
| 5,099,080 | 3/1992 | Quakenbush ......................... 568/934 |

*Primary Examiner*—James H. Reamer
*Attorney, Agent, or Firm*—F. A. Iskander

[57] ABSTRACT

Improved process for preparing dinitrotoluene by reacting toluene with concentrated nitric acid. The process reacts toluene with a large excess of concentrated nitric acid, in the presence of a select hydrated nitrate salt which is effective in minimizing explosive hazards, to produce a product which has substantially reduced by-product content.

14 Claims, No Drawings

PROCESS FOR PREPARING DINITROTOLUENE

FIELD OF THE INVENTION

This invention relates to a process for the production of dinitrotoluene (DNT). More particularly, the invention relates to an improved liquid-phase reaction of toluene with a stoichiometric excess of concentrated nitric acid at selected conditions to minimize explosion hazards and produce a product which has a substantially reduced by-product content.

BRIEF DESCRIPTION OF PRIOR ART

Commercial processes for preparing dinitrotoluene (DNT) react toluene with a mixed acid containing nitric and sulfuric acid. Mononitrotoluene (MNT) is produced first, followed by DNT formation. The nitration reaction is usually accompanied by minor oxidation side reactions resulting in the formation of small amounts of cresol and other phenolic by-products. Some of these undesirable by-products, such as dinitro-ortho-cresol, are highly toxic. These by-products are removed from the DNT by washing with alkaline water, which must then be treated to remove the toxic compounds before it is discharged into public waters.

Additionally, the use of mixed acid systems usually involves reconcentration of the spent sulfuric acid after the nitration reaction. This reconcentration step is time-consuming, energy-intensive and requires the use of expensive materials of construction.

In view of these disadvantages associated with mixed nitric/sulfuric acid systems, there have been several developments in the prior art to perform gas-phase or liquid-phase nitrations with concentrated nitric acid in the absence of sulfuric acid. U.S. Pat. No. 2,362,743 is illustrative of one such development wherein the nitration is carried out in two steps using different nitric acid concentrations.

U.S. Pat. No. 3,928,395 describes a process for nitrating aromatic compounds using 90 to 100% nitric acid in the optional and preferred presence of a dipolar aprotic solvent, the solvent being further used to dilute the reaction mixture and halt the reaction after the desired degree of nitration has been attained.

U.S. Pat. No. 3,957,889 describes an improved process for nitrating toluene or ortho-xylene with nitric acid, wherein the nitration rate is augmented by carrying out the reaction in the presence of an effective amount of anhydrous calcium sulfate or soluble anhydrite.

The use of molten nitrate salt in the gas-phase nitration of toluene with nitric acid to DNT is taught in U.S. Pat. No. 4,804,792. According to the patent, the molten salt serves as a temperature regulator for the reaction and as an isothermal medium for the reactants. A preferred method of contacting the reactants in the presence of the molten salt is by bubbling the reactants into a bath of the molten salt by means of a carrier gas such as nitrogen. The vapor phase reaction is carried out at a temperature of between 150° and 250° C.

U.S. Pat. No. 4,918,250 describes a process for nitrating toluene to DNT and phase separating the product using a nitrate salt as a phase separation agent. DNT is produced in a two-step liquid-phase nitration reaction, and the nitrate salt is then added to the mixture of DNT and unreacted nitric acid in an amount sufficient to cause phase separation of the mixture in order to facilitate isolation of the DNT from the unreacted nitric acid.

For additional teachings on the use of nitrate salt to facilitate the separation and recovery of DNT after completion of the nitration reaction, see also U.S. Pat. Nos. 5,001,272 and 5,099,079.

Generally speaking, the production of DNT by the liquid-phase reaction of toluene with nitric acid, to the exclusion of sulfuric acid, has one major drawback, namely, the formation of detonable solutions. For example, a typical liquid-phase nitration at about 40° C. using 9 moles of nitric acid per mole of toluene will produce a reaction product mixture which, if a sufficient mechanical shock is induced, would be susceptible to violent detonation.

The use of a large stoichiometric excess of nitric acid is one effective way of minimizing or eliminating the hazard of detonation. However, this is costly in that it would require more energy and the use of larger, more costly equipment in connection with recycling large amounts of excess or unreacted nitric acid.

SUMMARY OF THE INVENTION

This invention has two primary objectives in connection with the production of DNT by the liquid-phase reaction of toluene with nitric acid in the absence of sulfuric acid. The first is to minimize the hazards of explosion associated with such a reaction. The second objective is to produce DNT having a substantially reduced content of phenolic by-product, e.g., preferably less than 350 ppm of cresol. The attainment of these two combined objectives is critical to the successful commercialization of the nitric acid process (as distinguished from the mixed nitric/sulfuric acid process) for making DNT.

In accordance with the invention, it has been found that the foregoing objectives can be achieved under specified reaction conditions by employing a stoichiometric excess of nitric acid to toluene and carrying out the reaction in the presence of a hydrated nitrate salt. The salt serves as a diluent obviating the need for using large stoichiometric excesses of nitric acid to eliminate or minimize detonation hazards.

DETAILED DESCRIPTION OF THE INVENTION

More in detail, the nitration of toluene is effected using concentrated nitric acid. For example, acid concentrations of 60% or more by weight, based on the combined weight of the acid and water, may be used. Preferably, a concentration of 90% or greater is employed such as about 90 to 100%, preferably about 95 to about 99%, by weight.

The requirement of using a stoichiometric excess of the nitric acid reactant is critical to achieving a meaningful or sizable reduction in phenolic by-product formation, i.e., cresol and other undesirable phenolic by-products. Thus generally speaking, any molar excess of nitric acid may be employed that would be sufficient or effective to achieve the desired reduction of phenolic by-products.

The technique for measuring cresol by-product content of DNT is based on ultraviolet (U.V.) light absorbence. The by-products are extracted from the DNT sample with dilute sodium hydroxide washes. The absorbence of the extract is measured at 430 nm and compared to standards prepared using dinitro-ortho-cresol. Synthesis by-products are actually a mixture of cresols and phenolic compounds, but are all referenced against dinitro-ortho-cresol. Although different species will yield varying absorbences, this industry standard method gives a quantitative amount of the overall by-product content and quality of the measured sample. Typical industry standards for DNT require the cresol content measured with the U.V. absorbence method to be less than 350 ppm. DNT, made in a mixed acid system, typically has more than 1,000 ppm cresol content before washing.

Depending on other reaction parameters, the molar excess of nitric acid required may range, for example, upwards of 9 moles, preferably 10 or more moles (e.g., 10–22 moles), of nitric acid per mole of toluene. Obviously, because of economic considerations, no greater excess of nitric acid need or should be used than would be required to achieve the desired reduction in phenolic by-product formation. In accordance with the most preferred embodiments of the invention, to insure a sufficient reduction of phenolic by-products, from about 13 to about 18 moles, and still more preferably about 14 to about 17 moles of nitric acid are used per mole of toluene.

In accordance with the invention, the liquid-phase nitration of toluene with nitric acid is carried out in the presence of a hydrated nitrate salt. Illustrative such salts are the nitrates of lithium, calcium, manganese, magnesium, and zinc, and mixtures thereof. Specific illustrative hydrates of such salts include calcium nitrate tetrahydrate, lithium nitrate hydrate, manganese nitrate tetrahydrate, magnesium nitrate trihydrate, magnesium nitrate hexahydrate, zinc nitrate hexahydrate, mixtures thereof, and so forth. Generally, the hydrated nitrate salt is in aqueous solution form; or, if one starts out with an anhydrous or partially hydrated salt, when this is mixed with the nitric acid, it will absorb water and go into solution. Thus as used in the specification and claims herein, the term "hydrated nitrate salt" or "aqueous nitrate salt" is intended to mean any such salt which is in liquid or solution form or which becomes liquefied or solubilized in the reaction medium.

Any proportion of the nitrate salt may be used which is effective in reducing or eliminating the hazard of detonation without otherwise having any negative impact on the reaction or product thereof. Thus the term "effective amount", as used in the specification and claims herein, is intended to encompass any such amount. Obviously, the amount of nitrate salt used must not be so high as to materially affect or interfere with the rate of the nitration reaction. For example, an amount which results in substantial dilution of the reaction mixture or which brings about a phase separation before complete nitration of the toluene has taken place would effect a substantial reduction in the nitration rate. Such an amount would be obviously undesirable unless its negative effect on the reaction can be feasibly neutralized or minimized by proper manipulation or control of other reaction parameters. Usually, there is some interdependency between the level of stoichiometric excess of nitric acid used and the amount of nitrate salt which can be tolerated as having minimal or no effect on the reaction rate. For example, at higher ratios of acid to toluene, higher ratios of nitrate salt to toluene can be tolerated without adversely affecting the rate of reaction, and vice versa.

As another guideline in deciding on the effective amount of nitrate salt to be used in a particular reaction system, it has been found that optimum results obtain if the amounts of salt and of nitric acid used are such as to provide, upon completion of the nitration, a reaction product mixture in which the content of DNT is less than 15% by weight. Using this guideline, and with a predetermined molar ratio of nitric acid to toluene, one can then easily calculate the effective amount of nitrate salt to use in the reaction mixture.

By way of illustration, and without intending to be limited thereby, the effective amount of nitrate salt may range from about 0.1 to about 3.0 moles, and preferably from about 0.5 to about 2.5 moles, per mole of toluene. The most preferred range is from about 0.8 to about 2.0 moles of nitrate salt per mole of toluene.

The nitration reaction is effected at any suitable temperature such as from about 0° to about 80° C. Generally speaking, too high a reaction temperature may detrimentally affect the isomer distribution of the resulting dinitrotoluene, and this may be important when the resulting DNT is to be used, for example, as an intermediate for making toluene diamine and subsequently toluene diisocyanate. On the other hand, if one were to carry out the reaction at very low temperatures, this would require the use of costly chilling equipment or operations. Thus in accordance with the preferred embodiments, the nitration reaction is effected at a temperature ranging from about 35° to about 70° C. and still more preferably about 40°–60° C.

The process of the invention can be operated batch-wise or on a continuous basis, the continuous process being preferred. Typically in a continuous process, the nitric acid, to which has been added the requisite amount of hydrated nitrate salt, and toluene are continuously fed to a single reactor or a series of reactors. Since the nitration reaction is exothermic, cooling means is provided to remove some of the heat of reaction and thereby maintain the reaction mixture at or within the desired temperature. The nitration reaction proceeds step-wise beginning with the conversion of toluene to mononitrotoluene, the latter being further nitrated to dinitrotoluene. The residence time inside the reactor is determined as a function of the temperature. For example, at a temperature of about 40° C. a residence time of approximately 25 minutes is sufficient to bring about the conversion of all the toluene and substantially all the mononitrotoluene to DNT.

The DNT product can then be separated by any suitable means, such as phase separation and, thereafter, purified using conventional methods to achieve the desired degree of purity. Advantageously, the hydrated nitrate salt used in the nitration reaction may be increased, by the addition of more such salt to the reaction product mixture, to such levels as necessary to effect phase separation as taught for example in U.S. Pat. No. 4,918,250, No. 5,001,272 and No. 5,099,079.

The following examples are provided to illustrate the invention. In these examples, all parts and percentages are by weight unless otherwise specified.

EXAMPLE 1

In this example, a continuous stirred reactor operated at 50° C. was used. Toluene was fed to the reactor at 1.67 mls per minute concurrently with a feed stream at 13.9 mls per minute of a mixture of 98% nitric acid and a hydrated salt. The latter was a mixture of magnesium and zinc nitrate hydrate having the formula:

$$0.823 \; Mg(NO_3)_2 \cdot 0.177 \; Zn(NO_3)_2 \cdot 3.2 \; H_2O$$

The feed rate and composition of nitric acid/nitrate salt mixture was such as to provide 18 moles of the acid and 0.9 moles of the nitrate salt mixture per mole of toluene fed to the reactor. The conversion of toluene to DNT was complete in 30 minutes of residence time in the reactor. Product DNT was recovered from the reactor effluent by phase separation, water washed and analyzed by U.V. absorption for cresol content. It was found to contain 153 ppm by weight of cresol.

EXAMPLES 2-12

To illustrate the function of the hydrated nitrate salt in reducing the shock sensitivity of the DNT reaction product mixture, various test compositions were prepared which represented theoretical reaction product mixtures based on varying feed ratios of acid to toluene and hydrated nitrate salt to toluene. In each instance, the hydrated nitrate salt was the same one used in Example 1. The various compositions were then tested for shock sensitivity using 300 grams of each composition. In each test, the composition was placed in a cylindrical steel container 200 mm high with an outside diameter of 60 mm and an inside diameter of 50 mm. The container rested on a steel disk (diameter 40 mm, height 4.5 mm) which in turn rested on a cylindrical solid lead block 70 mm high by 40 mm diameter. The lead block was supported by another steel disk of the same dimension as the disk resting on top of the block. The cylindrical container was closed with a polypropylene lid having a hole through which a thin glass test tube was inserted containing 3 or 10 grams of a primer, namely, pentaerythritol tetanitrate (PETN). A remotely controlled electro-magnetic exploder was used to ignite the PETN.

In the case of each composition after each shot, the compression of the lead block was measured to access the detonability of each composition relative to the compression of pure liquid DNT (which is detonable) when the same quantity of primer is used. The make-up of each composition and the results of the relative compression test are provided in TABLE I below:

TABLE I

| Example No. | Liquid Composition Make-up (Weight %) | | | | Relative Compression* (%) |
|---|---|---|---|---|---|
| | Water | Nitric Acid | DNT | Nitrate Salt | |
| 2 | 25.7 | 7.6 | 1.4 | 65.3 | 3 |
| 3 | 19.1 | 26.7 | 9.7 | 44.5 | 43 |
| 4 | 19.1 | 26.7 | 9.7 | 44.5 | 30 |
| 5 | 22.7 | 7.1 | 12.4 | 57.6 | 33 |
| 6 | 11.0 | 56.7 | 13.6 | 18.7 | 57 |
| 7 | 11.0 | 56.7 | 13.6 | 18.7 | 57 |
| 8 | 12.0 | 52.2 | 15.1 | 20.7 | 100 |
| 9 | 12.0 | 52.2 | 15.1 | 20.7 | 60 |
| 10 | 12.0 | 52.2 | 15.1 | 20.7 | 65 |
| 11 | 10.4 | 57.6 | 16.7 | 15.3 | 110 |
| 12 | 10.4 | 57.6 | 16.7 | 15.3 | 147 |

*Relative compression to pure DNT which is 0%.

The data in TABLE I demonstrates: (a) that in the presence of nitric acid, a strong oxidizer, the energy output, as measured by compression, of the composition increased sharply as the DNT concentration increases, and (b) that with the proper dilution with hydrated nitrate salt, as well as acid and water, the energy output can be kept under control. Thus in the worst case, per Example 12, a relative compression which is 147% greater than that of pure DNT is still manageable and is on the borderline of the level of shock sensitivity that may be considered hazardous.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A process for the production of dinitrotoluene which comprises reacting, in the liquid phase, toluene with concentrated nitric acid, using at least 10 moles of nitric acid per mole of toluene, the reaction being carried out in the presence of a hydrated nitrate salt in an effective amount to reduce the hazard of detonation, the relative proportions of reactants and salt being such as to provide, upon completion of the reaction, a product mixture containing less than 15 percent by weight of dinitrotoluene.

2. The process of claim 1 wherein from 10 to 22 moles of nitric acid are used per mole of toluene.

3. The process of claim 2 wherein said reaction is carried out at a temperature from about 35° C. to about 70° C.

4. The process of claim 2 wherein the effective amount of said hydrated nitrate salt ranges from about 0.1 to about 3 moles per mole of toluene.

5. The process of claim 4 wherein said hydrated nitrate salt is a nitrate of a metal selected from the group consisting of lithium, calcium, manganese, magnesium, zinc, and mixtures thereof.

6. The process of claim 5 wherein from about 13 to about 18 moles of nitric acid are used per mole of toluene.

7. The process of claim 5 wherein said effective amount ranges from about 0.5 to about 2.5 moles per mole of toluene.

8. The process of claim 5 wherein said nitric acid has a concentration of at least 90 percent by weight.

9. The process of claim 8 wherein said temperature ranges from about 35° C. to about 70° C.

10. The process of claim 9 wherein from about 13 to about 18 moles of nitric acid are used per mole of toluene.

11. The process of claim 10 wherein said effective amount ranges from about 0.5 to 2.5 moles per mole of toluene.

12. The process of claim 11 wherein said hydrated nitrate salt is selected from the group consisting of calcium nitrate tetrahydrate, lithium nitrate hydrate, magnesium nitrate trihydrate, magnesium nitrate hexahydrate, zinc nitrate trihydrate, zinc nitrate hexahydrate, and mixtures thereof.

13. The process of claim 12 wherein said temperature is from about 40° C. to about 60° C.

14. The process of claim 13 wherein said hydrated nitrate salt is represented by the formula:

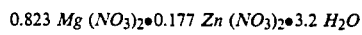

0.823 $Mg\ (NO_3)_2 \cdot 0.177\ Zn\ (NO_3)_2 \cdot 3.2\ H_2O$

* * * * *